(12) United States Patent
Henrich et al.

(10) Patent No.: US 11,287,130 B2
(45) Date of Patent: Mar. 29, 2022

(54) METHOD FOR REGULATING A GAS MIXTURE BY USING A GAS SENSOR AND A GAS MIXTURE SENSOR

(71) Applicant: ebm-papst Landshut GmbH, Landshut (DE)

(72) Inventors: Hartmut Henrich, Osnabrück (DE); Stephan Wald, Altenberge (DE); Jens Hermann, Osnabrück (DE)

(73) Assignee: ebm-papst Landshut GmbH, Landshut (DE)

( * ) Notice: Subject to any disclaimer, the term of this patent is extended or adjusted under 35 U.S.C. 154(b) by 0 days.

(21) Appl. No.: 16/746,030

(22) Filed: Jan. 17, 2020

(65) Prior Publication Data

US 2020/0232643 A1    Jul. 23, 2020

(30) Foreign Application Priority Data

Jan. 17, 2019 (DE) .......................... 102019101191.4

(51) Int. Cl.
*F23N 1/02* (2006.01)
*F23N 5/12* (2006.01)
*G01N 33/22* (2006.01)

(52) U.S. Cl.
CPC ............. *F23N 1/022* (2013.01); *F23N 5/123* (2013.01); *G01N 33/225* (2013.01)

(58) Field of Classification Search
None
See application file for complete search history.

*Primary Examiner* — Jason Lau
(74) *Attorney, Agent, or Firm* — Dickinson Wright PLLC

(57) ABSTRACT

A method for regulating a gas mixture formed from a gas and a fuel gas in a fuel gas-operated heating appliance, wherein the gas mixture is created by providing and mixing a gas quantity by way of a first control element and a fuel gas quantity by way of a second control element, wherein a microthermal gas sensor and a gas mixture sensor are used and sensor signals are relayed to a controller, and wherein upon change in the detected sensor signal [of the] gas sensor the newly detected sensor signal of the gas sensor is compared to reference values which have been measured in the laboratory and saved in a table of values in the controller and from this a target value of the sensor signal of the gas mixture sensor is determined without a mixture ratio of the gas mixture composed of fuel gas and gas being changed.

11 Claims, 4 Drawing Sheets

METHOD FOR REGULATING A GAS MIXTURE BY USING A GAS SENSOR AND A GAS MIXTURE SENSOR

RELATED APPLICATIONS

This application claims priority to German Application No. DE 10 2019 101 191.4, filed Jan. 17, 2019, the entire contents of which are incorporated herein by reference in their entirety.

FIELD

The disclosure relates to a method for regulating a gas mixture in a fuel gas-operated heating appliance.

BACKGROUND

Methods for regulating a gas mixture in a fuel gas-operated heating appliance are known in the prior art, for example, from the disclosure of document WO2006/000366A1.

Furthermore, a combustion regulation by the so-called SCOT method is known in the prior art, in which the control of the quantity of air supplied to the burner of the heating appliance is done in accordance with the burner capacity. A flame signal measurement is carried out by means of an ionization sensor and the mixture of gas and air is regulated to a target measured ionization value stored in a characteristic curve. However, we have found that it is a drawback in the SCOT method that the flame signal decreases too much when the burner capacity is low and thus the regulation becomes unreliable. Furthermore, the expense of the modification is large, especially when adapting the burner geometry, and the burner capacity can only be determined imprecisely in terms of the rotary speed of a fan furnishing the air volume flow for the mixture of gas and air.

Moreover, there is known in the prior art an electronic mixture regulation belonging to the patent applicant by using a thermal sensor for the gas mass flow. The sensor of the gas mass flow measures the fuel gas volume flow in the fuel gas and the nature of the fuel gas is determined by a controller from a reference table in terms of the thermal conductivity. The required air quantity is then calculated and regulated in accordance with the air demand so determined. However, this is complicated, since all of the input variables, i.e., the gas volume flow, the air volume flow, and the fuel gas properties need to be measured and hence monitored.

BRIEF SUMMARY

One problem which the disclosure proposes to solve is to provide a method for regulating a gas mixture in a fuel gas-operated heating appliance, which identifies changes in the properties of the gas added to the fuel gas and adapts regulating parameters in targeted manner.

This problem is solved by the combination of features according to claim 1.

According to the disclosure, a method is proposed for regulating a gas mixture formed from a gas and a fuel gas in a fuel gas-operated heating appliance, wherein the gas mixture is created by providing and mixing a gas quantity by way of a first control element and a fuel gas quantity by way of a second control element. A microthermal gas sensor, which detects at least one material property of the gas, is exposed to the gas and relays a sensor signal dependent on the particular gas to a controller. Furthermore, a microthermal gas mixture sensor, which detects at least one material property of the gas mixture, is exposed to the gas mixture and continuously relays a sensor signal dependent on the particular gas mixture to the controller. Upon change in the detected sensor signal of the gas sensor, the newly detected sensor signal of the gas sensor is compared to reference values which have been measured in the laboratory and saved in a table of values in the controller and from this a target value of the sensor signal of the gas mixture sensor is determined without a mixture ratio of the gas mixture composed of fuel gas and gas being changed.

In practice, it is generally the case with heating appliances that only the property of the gas, such as the relative humidity of the air, is changed without this producing a new mixture ratio for gas and fuel gas for a continued clean burning. Even so, the sensor signal of the gas mixture sensor changes on account of this change in the material property of the gas. To avoid a needless adjusting of the mixture ratio, the change in the material property of the gas is detected by the gas sensor and only the target value of the sensor signal of the gas mixture sensor is adapted. The mixture ratio of fuel gas and gas remains unchanged for this. The regulating of the gas mixture (ratio of fuel gas and gas) is then continued with the new target value of the sensor signal of the gas mixture sensor over the modulation range of the heating appliance.

This gas mixture regulation is based on a monitoring of the signal value of the gas mixture sensor. For this, the controller compares the continuously detected sensor signal of the gas mixture sensor to a target value of the sensor signal of the gas mixture sensor and upon deviation of the detected sensor signal of the gas mixture sensor from the target value of the sensor signal it actuates at least one of the first and second control elements so as to thereby adapt the gas mixture by increasing or decreasing the gas quantity and/or raising or lowering the fuel gas quantity until the target value of the sensor signal of the gas mixture sensor is reached.

An essential point is the measurement of the at least one material property of the gas mixture and the at least one material property of the gas. A change in the gas quantity or the fuel gas quantity would be identified at once by a change in the material properties at the gas mixture sensor. A change in the material properties of the gas mixture at the gas mixture sensor can be immediately compensated through the controller. A change in the material properties of the gas is detected at once in order to adapt the target value of the sensor signal of the gas mixture sensor.

The material property of the gas mixture detected by the microthermal gas mixture sensor is preferably the thermal conductivity and/or the temperature diffusivity of the gas mixture. However, several of these material properties may also be detected, so that a more precise coordination of the plurality of properties with the gas mixture is possible. The material property of the gas as detected by the microthermal gas sensor corresponds to those of the gas mixture sensor.

Another possibility is based on the functional principle of ultrasound measurement to determine the specific speed of sound dependent on the particular gas mixture. A corresponding sensor is likewise used as the gas sensor.

The method is characterized in one modification in that the target value of the sensor signal is adapted in dependence on a composition of the gas or the fuel gas by the controller. If the composition of the fuel gas changes (e.g., from propane to butane), the measured properties of the gas mixture will change. In addition, other compositions of fuel gas will also require other air quantities for an optimal combustion. Thus, a new mixture ratio between gas and fuel gas is also required.

Such an adapting of the target value of the sensor signal is done by a calibration process. For this, the first control element of the gas quantity or the second control element of the fuel gas quantity is changed by the controller until the desired result is achieved. The original target value is replaced by the new measured sensor signal for the further regulation of the mixture.

In particular, the calibration process is done by regulating the ionization current of a flame signal of a burner of the heating appliance until an ionization target value is reached. For this, at first a stoichiometric burning of the burner of the heating appliance is established. Through an ionization probe, the flame signal of the burner of the heating appliance and with this a corresponding ionization current is detected. During stoichiometric combustion, the ionization current is a maximum. From this value of the ionization current, an ionization target value is calculated with a percentage determined in the laboratory and this is stored for use as the future ionization current target value that must be reached for the desired combustion. After this, only the gas quantity is reduced by a predetermined factor in order to operate the burner with the desired gas mixture at the predetermined ionization target value.

The method is further characterized in that, upon reaching the ionization target value, the at least one material property of the gas mixture is measured by means of the gas mixture sensor and saved as a new target value of the sensor signal in the controller. The new target value is used for the further regulation and replaces the former target value.

The calibration process is done preferably in event of implausibilities of the sensor signal of the gas mixture sensor or in cyclical predetermined intervals. The determination of implausibilities of the sensor signal in one embodiment occurs upon starting of the heating appliance by first of all supplying only the known gas and exposing the gas mixture sensor to it. An implausibility is then present if the sensor signal of the material property, such as the thermal conductivity or the temperature diffusivity, as measured by the gas mixture sensor, does not match a sensor signal for the known gas. The gas in the case of heating appliances is usually the surrounding air, whose material properties are known.

Different kinds of fuel gas or families of fuel gas (natural gas, liquefied gas) influence the material properties of the gas mixture in different ways. For example, the thermal conductivity decreases when liquefied gas is added to air, and the thermal conductivity increases when natural gas is added to air. In one modification of the method, it is therefore provided that at first only the known gas is supplied, preferably air, and the gas mixture sensor is exposed to it. Then the fuel gas is supplied, the gas mixture is created, and the gas mixture sensor is exposed to the gas mixture. The nature of the fuel gas is determined from the change in the sensor signal when the fuel gas is supplied. The controller then adapts the gas mixture in dependence on the ascertained nature of the fuel gas until the target value of the sensor signal is reached. In this way, the starting power can be controlled by the controller immediately after identifying the gas family by positioning the control element of the fuel gas at a favorable starting point and the ignition mixture is achieved more quickly and precisely at the starting of the burner.

The method moreover takes advantage of the above described effect of the increasing or decreasing of the sensor signal in the case of different fuel gases and proposes that the direction of action of the regulating process is detected from the change in the sensor signal when the fuel gas is supplied and from this it is determined whether the supplied fuel gas quantity is increased or decreased in order to reach the target value of the sensor signal. The goal is always a clean burning with the gas mixture required for this.

The gas is preferably air, the fuel gas is preferably liquefied gas or natural gas, or any desired fuel gas mixture.

One modification of the method moreover involves an embodiment in the event that the thermal properties of the fuel gas are too close to the thermal properties of the air and no reliable regulation of the mixture is possible, since any change in either the air quantity or the gas quantity will not bring about any signal change at the gas mixture sensor. This may occur, for example, when mixed fuel gases are used for the burning. This status is recognized by the controller, both upon starting the heating appliance and during a calibration, by a plausibility check, when no significant change in the sensor signal is measured upon any given change in the air or the gas quantity. In this case, the controller can temporarily switch off the regulating of the mixture via the gas mixture sensor and control the process with reduced modulation range solely by the regulating of the ionization current as described for the calibration. Once the fuel gas quality again makes possible a regulation through the gas mixture sensor positioned in the gas mixture, the regulating of the mixture through the gas mixture sensor continues.

In one variant embodiment, it is provided that the material properties of the gas as detected by the gas sensor are checked continually for changes and the controller continually adapts the target value of the sensor signal of the gas mixture sensor.

BRIEF DESCRIPTION OF THE DRAWINGS

Other advantageous modifications of the disclosure are characterized in the dependent claims or shall be presented more closely in the following along with the description of the preferred embodiment of the disclosure with the aid of the figures. There are shown:

DETAILED DESCRIPTION

Figure 1:
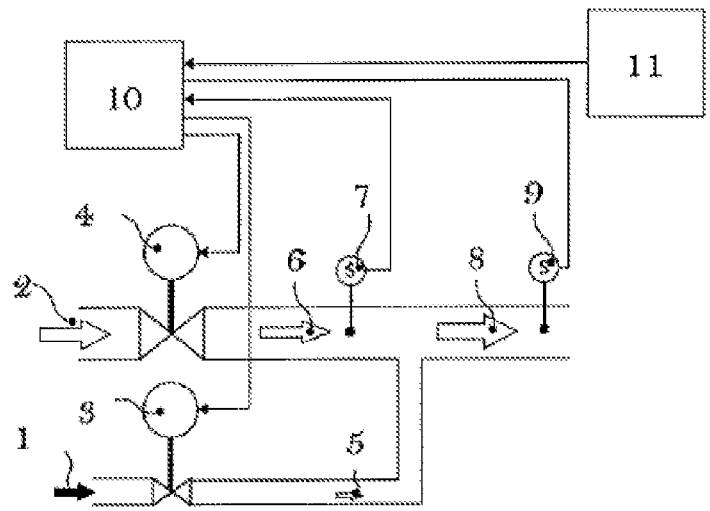
FIG. 1 a basic layout to carry out the method.

FIG. 1 shows a basic layout to carry out the method. In the following description of the figures, air is assumed to be the gas, even though in theory other gases can also be used.

Through the controller 10, the control element 4 for the feeding of a controllable quantity of air 2 and the control element 3 for feeding a controllable quantity of fuel gas 1 are regulated in their respective opening positions in order to create the gas mixture 8 in a particular mixture ratio of fuel gas and air. In the area of the gas mixture 8 there is positioned the gas mixture sensor 9, which is exposed to the gas mixture 8. In the area of the regulated air 6 there is positioned the gas sensor 7, which is exposed solely to air. The air regulated in its quantity and the fuel gas 5 regulated in its quantity are mixed homogeneously in the area of the gas mixture sensor 9. Each of the two sensors 7, 9 is designed to measure the physical material properties, such as the thermal conductivity, the temperature diffusivity and (with other sensors) the speed of sound. Through a process monitoring unit 11, the controller 10 and the regulation process are monitored. Furthermore, the signal lines to and from the controller 10, which processes the regulating of the gas mixture 8, are shown by arrows.

Figure 2:
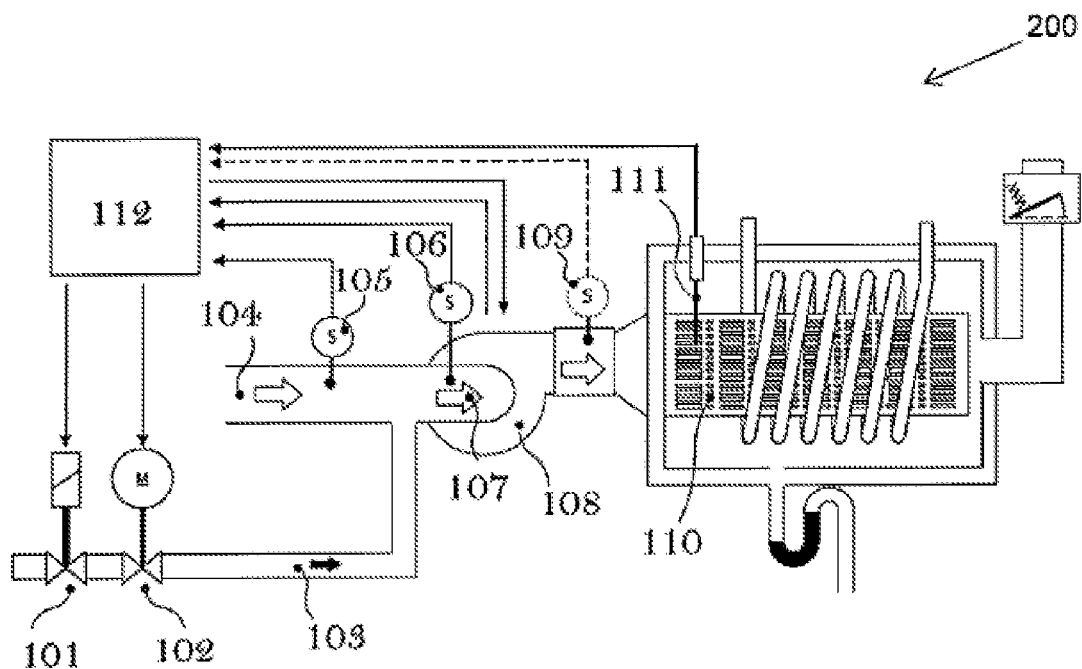
FIG. 2 a layout of a heating appliance to carry out the method.

FIG. 2 shows a specific embodiment of a fuel gas-operated heating appliance 200 with a gas safety valve 101, a gas regulating valve 102 as the control element for the quantity of fuel gas 103, a mixed flow fan 108 to draw in air 104 and to mix it with the fuel gas 103 to create the gas mixture 107. The air quantity can be adjusted through the rotary speed of the mixed flow fan 108; hence, it constitutes the control element for the air supply. The heating appliance 200 comprises the microthermal gas mixture sensor 106, while a second gas mixture sensor 109 is depicted as an alternative installation position in the outflow area of the mixed flow fan 108. Basically, however, no second gas mixture sensor is required. The heating appliance 200 moreover comprises the microthermal gas sensor 105 in the air supply area. The mixed flow fan 108 delivers the gas mixture 107 to the burner 110, on which the ionization electrode 111 is installed, in order to monitor the burner flame. Furthermore, arrows show the signal lines to and from the controller 112, which processes the regulating of the gas mixture 107.

In the following, the components of the basic layout of FIG. 1 shall be discussed, although they are directly applicable to the heating appliance 200 of FIG. 2.

Figure 3:
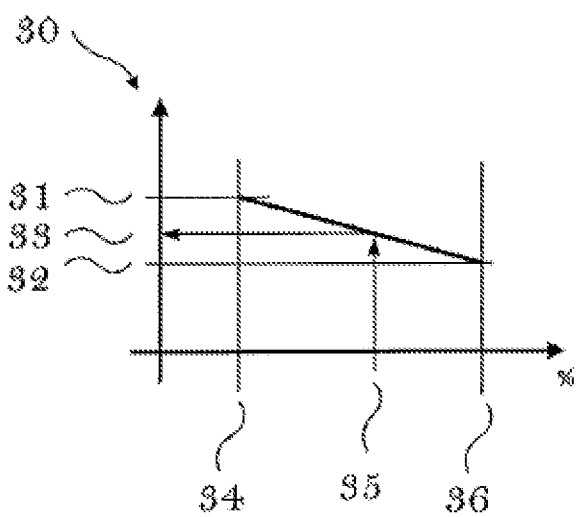
FIG. 3 a regulation characteristic of the sensor signal of the gas mixture sensor.

FIG. 3 shows a diagram 30 of a simplified linear relationship between the sensor signal 31 detected by the gas mixture sensor 9 in the case of pure air 2 (reference number 34 corresponds to 100% air) and the sensor signal 32 in the case of pure fuel gas 1 (reference number 36 corresponds to 100% fuel gas), which is used for the regulation. The sensor signal 33 lies in between these for the gas mixture 8 (reference number 35 corresponds to 60% air and 40% fuel gas). The quantities of air 2 and fuel gas 1 are adjusted with the respective control elements 3 and/or 4 until such time as the mixture properties of the desired mixture ratio required by the process have been detected by the gas mixture sensor 8. FIG. 3 shows a linear trend of the characteristic curve of the sensor signal, but nonlinear curves are also possible, enabling for example a regulation for corresponding positions of the control elements 3, 4 by using tables of values.

Figure 4:
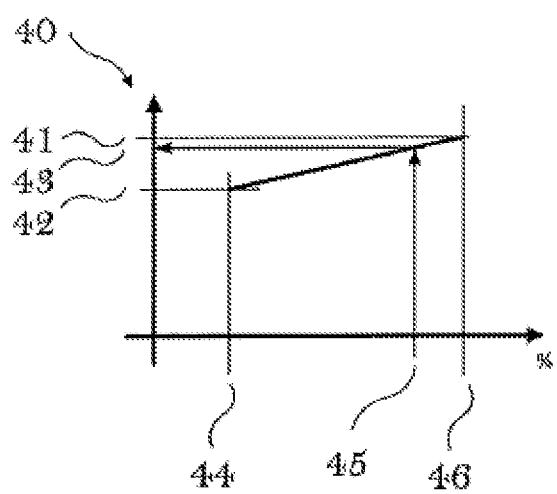
FIG. 4 a regulation characteristic of the sensor signal of the gas mixture sensor.

According to FIG. 3, the sensor signal decreases as more fuel gas 1 is added. For example, the sensor signal is represented as being dependent on the thermal conductivity as the material property of the gas mixture 8, where the fuel gas is a liquefied gas for example and the thermal conductivity of liquefied gas is lower than that of air. However, there are also kinds of gases for which the direction of the regulating action is reversed, as shown in FIG. 4. Here, the fuel gas 1 is natural gas, whose thermal conductivity is higher than that of air. In the diagram 40 of FIG. 4, there is shown a simplified linear relationship between the sensor signal 41 detected by the gas mixture sensor 9 in the case of pure air 2 (reference number 44 corresponds to 100% air) and the sensor signal 42 in the case of pure fuel gas 1 (reference number 46 corresponds to 100% fuel gas/natural gas), which is used for the regulation. The sensor signal 43 lies in between these for the gas mixture 8 (reference number 45 corresponds to 75% air and 25% fuel gas/natural gas), but is close to the sensor signal 41 of pure fuel gas 1. For a regulation with natural gas, the controller 10 determines the direction the regulating action from the signal change of the gas mixture sensor 9 upon increase in the fuel gas quantity and uses this for the further regulating of the mixture.

Figure 5:
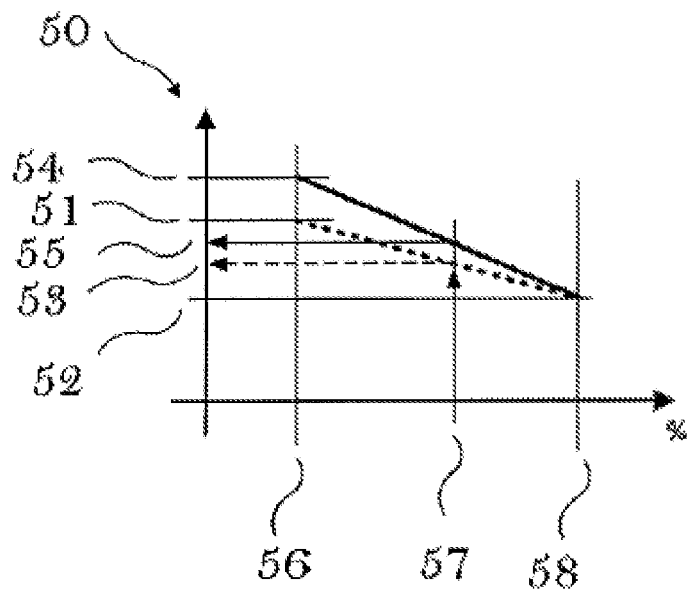
FIG. 5 regulation characteristics before and after a change in the gas properties.

The determination of the target value of the sensor signal of the gas mixture sensor 10 is shown schematically in the diagram 50 of FIG. 5. From the material property measured by the gas sensor 7, such as a change in the relative humidity, a new sensor signal target value is ascertained. The mixture ratio 57 of fuel gas 2 and air 1 remains unchanged, however. For example, in the case of pure air 1 (reference number 56 corresponds to 100% air; reference number 58 to pure fuel gas), if the sensor signal changes, e.g., upon change in the relative humidity, from the original value (reference number 51) to a new value (reference number 54), the controller 11 will extrapolate the mixture sensor target value from the old value (reference number 53) to the new value (reference number 55), making use of the signal value of the gas sensor 7, or correct it with values from a table of values stored in the controller 11. Reference numbers 52 and 54 designate the sensor signals for pure air and pure fuel gas, respectively.

Figure 6:
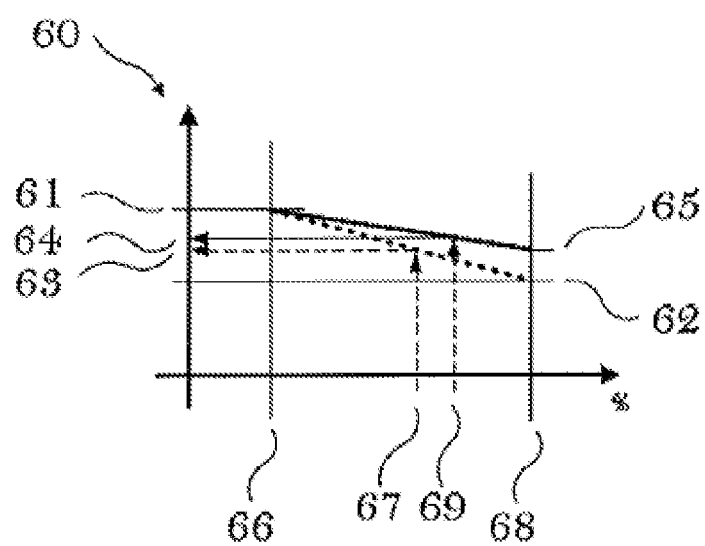
FIG. 6 regulation characteristics before and after a change in the fuel gas properties.

FIG. 6 shows a diagram 60 representing the calibration, for example when the nature of the fuel gas 1 changes so much that a new gas mixture composition is required in order to assure an optimal combustion. In FIG. 6, for example, the fuel gas changes from propane to butane. Reference numbers 66 and 68 determine the range between 100% air and 100% fuel gas, the signal value 61 being 100% air. During the calibration, the gas mixture 8 is changed from the original mixture ratio 67 with the corresponding signal value 63 to the new mixture ratio 69 with the corresponding signal value 64. By the detection of the material properties of both the air 2 and the fuel gas 1 through a respective suitable sensor, the direction of the regulating action can be predetermined and the gas mixture 8 can be preset for the subsequent regulating of the fuel gas quantity and/or the air quantity. FIGS. 5 and 6 show the situation of the original nature of the fuel gas by broken line, the new situation by solid lines and arrows.

Figure 7:
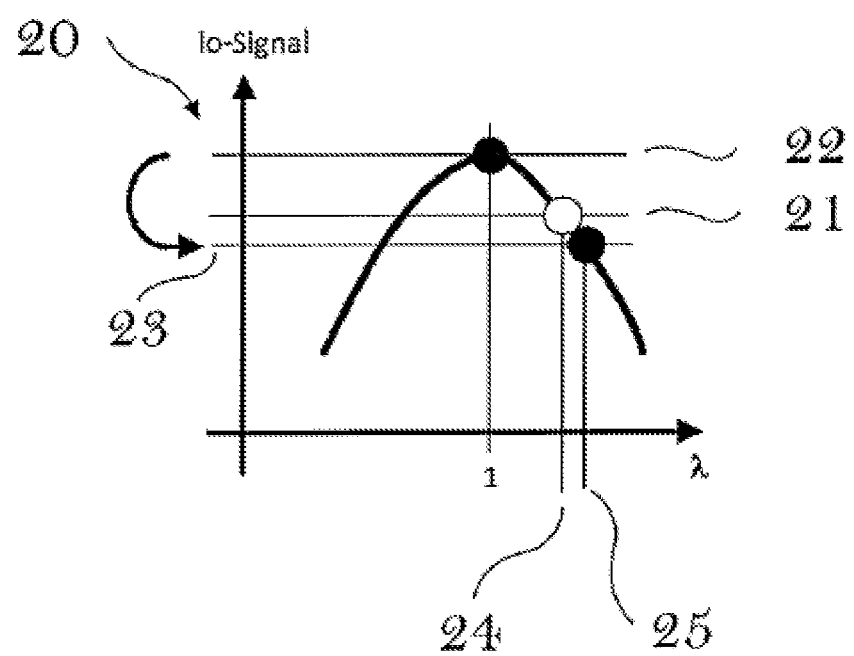
FIG. 7 a characteristic of the ionization current regulation.

FIG. 7 shows a diagram 20 for the calibration by means of regulating the ionization current with a characteristic curve of the ionization signal (lo-signal) detected by the ionization electrode in the burner flame with respect to the ratio λ of fuel gas and air. Since the basic layout of FIG. 1 shows no ionization electrode, in the following we shall refer to the heating appliance 200 of FIG. 2. The controller 112 controls the quantity of air 105 to a given value during the operation of the burner, the ionization signal at the ionization electrode 111 of the burner 110 is measured, and the quantity of fuel gas 103 is increased until the ionization signal has increased from the originally present ionization value 21 for a fuel gas and air ratio 24 to the maximum 22. From this value, using a percentage determined in the laboratory, the ionization target value 23 is calculated and saved as the future ionization current target value which must be reached by the desired ratio of fuel gas and air 25 with larger air surplus.

The invention claimed is:
1. Method for regulating a gas mixture formed from a gas and a fuel gas in a fuel gas-operated heating appliance, wherein the gas mixture is created by providing and mixing a gas quantity by way of a first control element and a fuel gas quantity by way of a second control element, wherein a microthermal gas sensor, which detects at least one material property of the gas, is exposed to the gas and relays a sensor signal dependent on a particular gas to a controller, wherein a microthermal gas mixture sensor, which detects at least one material property of the gas mixture, is exposed to the gas mixture and continuously relays a sensor signal dependent on the particular gas mixture to the controller, wherein, upon change in the detected sensor signal of the gas sensor, a newly detected sensor signal of the gas sensor is compared with reference values which have been measured in the laboratory and saved in a table of values in the controller and from this a target value of the sensor signal of the gas mixture sensor is determined without a mixture ratio of the gas mixture composed of fuel gas and gas being changed, wherein the target value of the sensor signal of the gas mixture sensor is adapted in dependence on a composition of the gas or the fuel gas by the controller, and wherein the adapting of the target value of the sensor signal of the gas mixture sensor is done by a calibration process including regulating the ionization current of a flame signal of a burner of the heating appliance until an ionization target value is reached.

2. Method according to claim 1, wherein the controller compares the continuously detected sensor signal of the gas mixture sensor with a target value of the sensor signal of the gas mixture sensor and upon deviation of the detected sensor signal of the gas mixture sensor from the target value of the sensor signal it actuates at least one of the first and second control elements and thereby adapts the gas mixture by increasing or decreasing the gas quantity and/or raising or lowering the fuel gas quantity until the target value of the sensor signal of the gas mixture sensor is reached.

3. Method according to claim 1, wherein the material property of the gas mixture detected by the microthermal gas mixture sensor is/are the thermal conductivity and/or the temperature diffusivity of the gas mixture.

4. Method according to claim 1, wherein the material property of the gas detected by the microthermal gas sensor is/are the thermal conductivity and/or the temperature diffusivity of the gas.

5. Method according to claim 1, wherein upon reaching the ionization target value, the at least one material property of the gas mixture is measured by means of the gas mixture sensor and saved as a new target value of the sensor signal in the controller.

6. Method according claim 1, wherein the calibration process is done in the event of implausibilities of the sensor signal of the gas mixture sensor or in a cyclical manner.

7. Method according to claim 6, wherein a determination of the implausibilities of the sensor signal is done at the starting of the heating appliance by first of all supplying only the known gas and exposing the gas mixture sensor to it, whereupon an implausibility is present if the sensor signal as measured by the gas mixture sensor does not match a sensor signal for the known gas.

8. Method according to claim 1, wherein upon starting the heating appliance at first only the known gas is supplied and the gas mixture sensor is exposed to it, and then the fuel gas is supplied, the gas mixture is created, and the gas mixture sensor is exposed to the gas mixture, whereupon the nature of the fuel gas is determined from a change in the sensor signal when the fuel gas is supplied, and the controller adapts the gas mixture in dependence on the ascertained nature of the fuel gas until the target value of the sensor signal is reached.

9. Method according to claim 8, wherein the direction of action of the regulating process is detected from the change in the sensor signal when the fuel gas is supplied and from this it is determined whether the supplied fuel gas quantity is increased or decreased in order to reach the target value of the sensor signal.

10. Method according to claim 8, wherein the material properties of the gas as detected by the gas sensor are checked continually for changes and the controller continually adapts the target value of the sensor signal of the gas mixture sensor.

11. Method according to claim 1, wherein the gas is air and the fuel gas can be chosen arbitrarily.

* * * * *